(12) United States Patent
Saruhashi et al.

(10) Patent No.: US 6,478,960 B1
(45) Date of Patent: *Nov. 12, 2002

(54) MANUFACTURING METHOD OF ARTIFICIAL ORGAN, HOLLOW FIBER, AND DIALYZER OF HOLLOW FIBER MEMBRANE TYPE

(75) Inventors: Makoto Saruhashi, Kanagawa-ken (JP); Masatomi Sasaki, Kanagawa-ken (JP)

(73) Assignee: Asahi Medical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/213,871

(22) Filed: Dec. 17, 1998

(30) Foreign Application Priority Data

Dec. 17, 1997 (JP) .............................. 9-347489
Jun. 9, 1998 (JP) .......................... 10-161162

(51) Int. Cl.$^7$ ............................. B01D 63/02
(52) U.S. Cl. ................ 210/500.23; 210/321.8; 210/321.89; 210/500.24
(58) Field of Search ...................... 210/500.23, 500.24, 210/321.8, 321.89

(56) References Cited

U.S. PATENT DOCUMENTS

| | | | |
|---|---|---|---|
| 3,615,024 A | | 10/1971 | Michaels |
| 4,389,363 A | * | 6/1983 | Molthop .................... 264/135 |
| 4,454,085 A | | 6/1984 | Schindler et al. |
| 4,787,974 A | * | 11/1988 | Ambrus et al. .......... 210/321.8 |
| 4,804,382 A | | 2/1989 | Turina et al. |
| 4,872,982 A | | 10/1989 | Taylor |
| 5,160,672 A | | 11/1992 | Sasaki et al. |
| 5,387,345 A | | 2/1995 | Dünweg et al. |
| 5,489,303 A | * | 2/1996 | Sasaki et al. ................ 623/11 |
| 5,762,798 A | * | 6/1998 | Wenthold et al. |

FOREIGN PATENT DOCUMENTS

| | | |
|---|---|---|
| DE | 3636735 | 5/1988 |
| DE | 19511151 | 10/1996 |

(List continued on next page.)

OTHER PUBLICATIONS

Israel Cabasso et al., *Polysufone Hollow Fibers. I. Spinning and Properties*, Journal of Applied Polymer Science, vol. 20, 2377–2394 (1976).

Israel Cabasso et al., *Polysulfone Hollow Fibers. II. Morphology*, Journal of Applied Polymer Science, vol. 21, 165–180 (1977).

*Primary Examiner*—John Kim
(74) *Attorney, Agent, or Firm*—Burns, Doane, Swecker & Mathis, LLP

(57) ABSTRACT

A manufacturing method of an artificial organ formed of a material having a solubility parameter δ of not more than 13 $(cal/cm^3)^{1/2}$ involves filling micropores of the body fluid treatment membrane with a filling solution having no or little solubility with respect to a fat-soluble modifier solution, and coating a portion of the body fluid treatment membrane with the fat-soluble modifier by contacting the fat-soluble modifier solution. With this method substantially only the necessary portions need to be coated with the fat-soluble modifier so that a smaller amount of the fat-soluble modifier may be employed. A microporous membrane is formed of a synthetic polymer substrate having a solubility parameter δ of not more than 13 $(cal/cm^3)^{1/2}$, with not less than 50 wt % of fat-soluble modifier included in the hollow fiber membrane being held on a surface which may contact body fluid. The membrane possesses the following sieve coefficients measured by dextrans: no more than 0.4 when a dextran with a molecular weight of 100,000 is employed; and not less than 0.5 when another dextran with a molecular weight of 10,000 is employed.

2 Claims, 1 Drawing Sheet

FOREIGN PATENT DOCUMENTS

| | | |
|---|---|---|
| DE | 19526383 | 1/1997 |
| EP | 168783 | 1/1986 |
| EP | 0345151 | 12/1989 |
| EP | 0351773 | 1/1990 |
| EP | 615778 | 9/1994 |
| EP | 749775 | 12/1996 |
| JP | 57-71409 | 5/1982 |
| JP | 57-71410 | 5/1982 |
| JP | 57-71411 | 5/1982 |
| JP | 57-071408 | 5/1982 |
| JP | 57-199808 | 12/1982 |
| JP | 07-178166 | * 7/1995 |
| WO | 96/17675 | * 6/1996 |

* cited by examiner

MANUFACTURING METHOD OF ARTIFICIAL ORGAN, HOLLOW FIBER, AND DIALYZER OF HOLLOW FIBER MEMBRANE TYPE

BACKGROUND OF THE INVENTION

The present invention relates to manufacturing methods of artificial organs including microporous membranes for treating body fluid. The microporous membranes, which are formed of hydrophobic materials, have portions coated with a fat-soluble modifier. More particularly, the present invention pertains to manufacturing methods of artificial organs, such as, dialyzers, oxygenators, and plasma separation apparatus. Such artificial organs have excellent biocompatibility by inhibiting activation of blood constituents such as leukocytes, and platelets.

Moreover, the present invention relates to hollow fiber membranes, and dialyzers of hollow fiber membrane type, which are each excellent in removal of substances having middle molecular-weight. More particularly, the present invention pertains to hollow fiber membranes, and dialyzers of hollow fiber membrane type, which are each biocompatible by inhibiting activation of blood constituents such as leukocytes, and platelets.

Generally, synthetic macromolecular membranes have been widely used as dialysis membranes, and blood constituent separation membranes to be used in artificial organs, such as dialyzers, and plasma separators. However, when a patient undergoes a blood dialysis treatment with a dialyzer, a frequent extracorporeal circulation is needed. This often brings about complications caused by activation of blood constituents, and casts a serious problem to the patient. Particularly when patients who have taken a dialysis treatment for a long period of time, lowering of anti-oxidation of blood constituents, and high content of lipid peroxide in blood are observed in these patients. Such patients are in many cases affected with arterial sclerosis.

In order to solve the problems, an artificial organ having a dialysis membrane with a surface coated with vitamin E, is proposed (JP-B-62-41738). In this case, the vitamin E possesses experts various physiological activities, such as intracorporeal anti-oxidation, stabilization of biomembranes, and inhibition of platelet coagulation. Highly unsaturated fatty acids such as eicosapentaenoic acid are also expected to exert antithrombotic activity and to improve hyperlipemia.

The above mentioned instances are concerned with a technology to treat a surface of a portion of body fluid treatment membrane, which contacts body fluid. On the other hand, another technology to increase hydrophobic properties of a portion of body fluid treatment membrane, which does not contact body fluid, has also been known. The membrane according to the latter technology adsorbs hydrophobic substances present in a dialysis liquid effectively so that invasion of those hydrophobic substances into body fluid is prevented.

However, when fat-soluble substances such as vitamin E are applied as a modifier for artificial organ materials, which are hydrophilic, the binding strength is weak between a fat-soluble substance and an artificial organ material. This causes a problem that the fat-soluble substance is peeled off the artificial organ material or is eluted.

Solubility parameter $\delta$ is known as an indicator of hydrophilicity of a material. The higher the value of $\delta$ is, the higher the hydrophilicity of the material is. Blood was circulated for 30 minutes in an artificial organ formed by a hydrophilic material, i.e., regenerated cellulose ($\delta=15.65$ $(cal/cm^3)^{1/2}$) having a surface coated with vitamin E. It was observed that about 90% of vitamin E on the surface of the regenerated cellulose has been eluted into blood.

A hydrophobic material, for example, having a $\delta$ value of at most 13 $(cal/cm^3)^{1/2}$ is used and coated with vitamin E. The whole area of the membrane is non-selectively coated with vitamin E, as far as a vitamin E solution is applied to the membrane according to a method described in JP-B-62-41738. In the above method, a CFC (chlorflourocarbon), n-hexane, or an alcohol is employed as a solvent, since all of them are inert to a dialysis membrane and dissolve vitamin E. These solvents easily enter pores of hydrophobic porous membrane. Therefore, vitamin E is dispersed all over the inner, middle, and outer surfaces of the membrane and deposited on these portions non-selectively. It is difficult to control the quantity of vitamin E to be deposited on the surfaces of the membrane, since vitamin E is deposited even on an area, which does not contact body fluid. Moreover, ability of the membrane to treat fluid such as body fluid is decreased, since the membrane is coated with vitamin E all over the surface and is changed to be more hydrophobic.

Generally, substances with molecular weight of about 100 have been removed by dialysis treatments. However, a recent dialysis treatment has enabled to remove not only these substances, but also so-called uremic middle molecular-weight substances with a molecular weight of between 100 and 5,000, and even $\beta$2-microglobulin with a molecular weight of 11,800 ($\beta$2-MG). Thus, it is now possible for a patient to improve complications caused by a long dialysis treatment. Manufacture of a larger pore-sized membrane than that ordinarily used by utilizing synthetic polymers such as polysulfones and polyamides has been under study (EP 168783, EP 82433). The membrane may remove larger molecular-weight substances by allowing them to pass through the larger pore-sized membrane. However, the larger pore-sized membrane has similar problems as those of an ordinary pore-sized membrane, as described above, if the larger pore-sized membrane is put to use in fabricating artificial organs to treat body fluid.

BRIEF SUMMARY OF THE INVENTION

Accordingly, it is an objective of the present invention to solve the above mentioned problems by providing a manufacturing method of an artificial organ having microporous body fluid treatment membranes, which are made of a hydrophobic material and include a portion coated with a fat-soluble modifier. Another objective of the present invention is to provide a manufacturing method of an artificial organ such as a dialyzer, an oxygenator, or a plasma separation apparatus. The artificial organ inhibits activation of blood constituents such as leukocytes and platelets, and has excellent biocompatibility. A further objective of the present invention is to provide a hollow fiber membrane and a blood dialysis apparatus having the hollow fiber membranes. The hollow fiber membrane has excellent properties in removing substances with middle molecular-weight and has a concentrated fat-soluble modifier on a surface, which may contact body fluid. To achieve the above objectives, the present invention provides the following:

(1) A manufacturing method of an artificial organ comprises a microporous body fluid treatment membrane, which is formed of a material with a solubility parameter $\delta$ of not more than 13 $(cal/cm^3)^{1/2}$ and has a portion coated with a fat-soluble modifier. The manufacturing further comprises the steps of:

filling micropores of the body fluid treatment membrane with a filling solution, which has no or little solubility with a fat-soluble modifier solution; and
coating a portion of the membrane to be coated with a fat-soluble modifier by contacting the fat-soluble modifier solution;

(2) The manufacturing method according to the method of (1), further comprising the step of removing the filling solution between the filling process and the coating process, wherein the filling solution is present on a surface of the portion of the membrane to be coated with the fat-soluble modifier;

(3) The manufacturing method according to the method of (1) or (2), wherein the coating process is to hold the fat-soluble modifier solution on the body fluid treatment membrane;

(4) The manufacturing method according to the method of any one of (1) to (3), wherein the fat-soluble modifier is vitamin (5) The manufacturing method according to the method of any one of (1) to (4), wherein the filling solution is water;

(6) The manufacturing method according to the method of any one of (1) to (5), wherein a portion to be coated with the fat-soluble modifier is a surface portion of the body fluid treatment membrane, which may contact body fluid;

(7) The manufacturing method according to the method of any one of (1) to (5), wherein the portion to be coated with the fat-soluble modifier is a surface portion of the body fluid treatment membrane, which may not contact body fluid;

(8) A hollow fiber membrane comprising a microporous hollow fiber membrane having a surface, which may contact body fluid, and which includes a fat-soluble modifier, wherein
not less than 50 wt % of fat-soluble modifier included in the hollow fiber membrane is held on a surface, which may contact body fluid; and
sieve coefficients measured by dextrans are:
not more than 0.4 when a dextran with a molecular weight of 100,000 is employed; and
not less than 0.5 when another dextran with a molecular weight of 10,000 is employed;

(9) The hollow fiber membrane according to the membrane of (8), wherein the hollow fiber membrane is formed of a synthetic polymer substrate having a solubility parameter δ of not more than 13 $(cal/cm^3)^{1/2}$;

(10) The hollow fiber membrane according to the membrane of (8) or (9), wherein the fat-soluble modifier is a fat-soluble vitamin;

(11) A dialyzer comprising a hollow fiber membrane, a body fluid passage, and a dialysis fluid passage, wherein a body fluid flowing in said body fluid passage contacts a dialysis fluid flowing in said dialysis fluid passage through said membrane so that a spodogenous substance in said body fluid is transferred into said dialysis fluid and removed, wherein said hollow fiber membrane is the membrane of any one of (8) to (10); and

(12) The dialyzer of hollow fiber membrane type according to the dialyzer of (11), wherein the artificial organ is obtained by the manufacturing method of the artificial organ according to the method of any one of (1) to (6).

BRIEF DESCRIPTION OF THE DRAWING

The features of the present invention, which are believed to be novel are set forth with particularity in the appended claims. The invention, together with objects and advantages thereof, may best be understood by reference to the following description of the presently preferred embodiments together with the accompanying drawing in which:

DETAILED DESCRIPTION OF THE PREFERRED EMBODIMENTS

Figure 1:
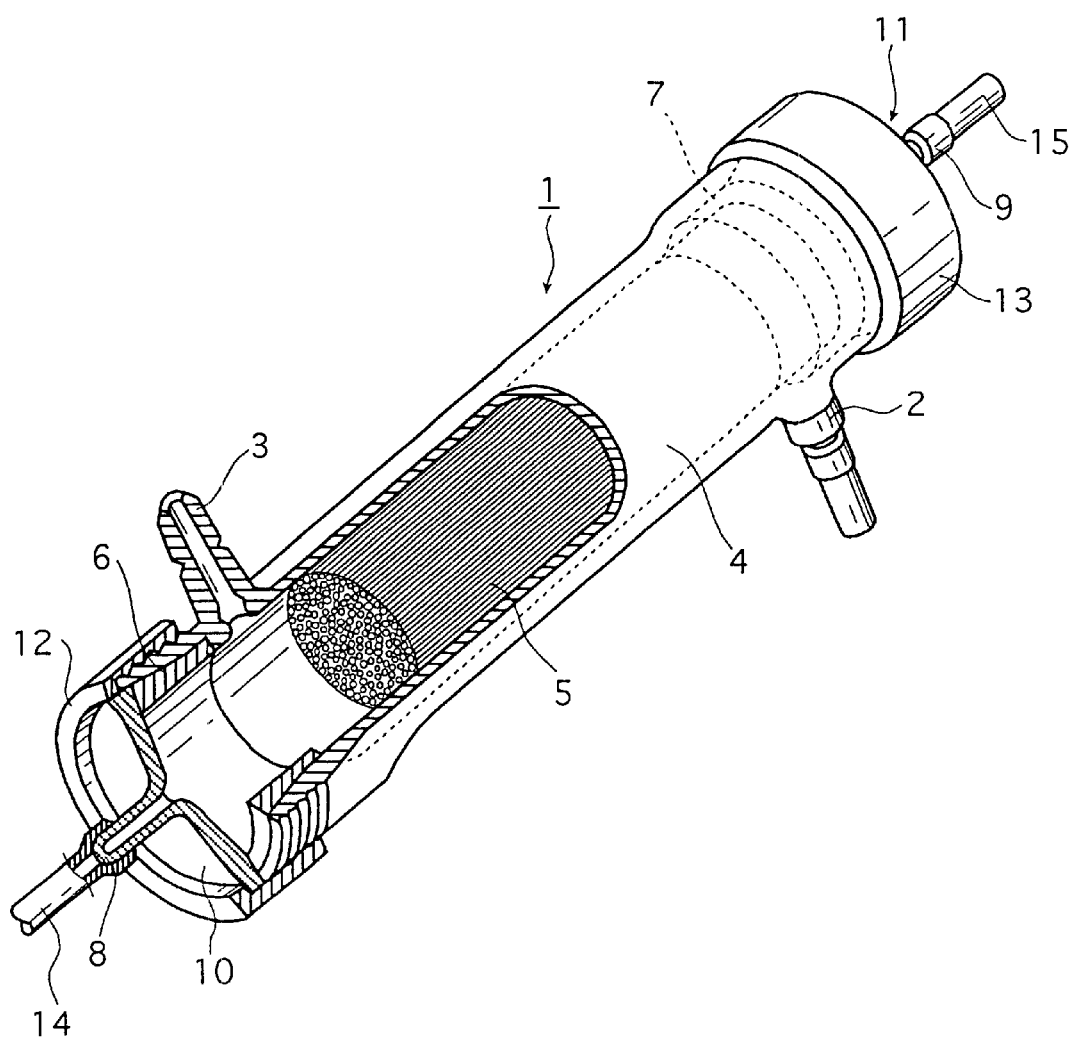
FIG. 1 is a partial cutaway perspective view showing a dialyzer of an embodiment of the present invention.

An artificial organ of the present invention is such as a dialyzer, an oxygenator, or a plasma separation apparatus. The dialyzer comprises body fluid treatment membrane, such as a dialysis membrane or a hemofiltration membrane, having micropores each with a pore size of from 1 nm to 20 nm diameter, preferably from 1 nm to 10 nm diameter on a portion, which substantially affects properties of the membrane such as selective permeability, and permeation rate. The dialyzer has a filtering function to remove spodogenous substances present in blood in a manner that the dialyzer transfers them into the outside of blood. Therefore, the body fluid treatment membrane used in the dialyzer is concerned with mass transfer between dialysis solution and body fluid (blood) defined by the membrane. The body fluid treatment membrane used in the dialyzer is a hydrophilic membrane represented by regenerated cellulose, or a hydrophobic membrane represented by polysulfone resin.

FIG. 1 shows an example illustrative of a kind of a dialyzer of hollow fiber membrane type. A cylindrical body 4 has an inlet tube 2 and an outlet tube 3 for dialysis solution arranged each in the proximity of each end of the cylindrical body 4. A number of hollow fiber membranes make a bundle 5 of hollow fiber membranes. The dialyzer 1 is fabricated by first inserting the bundle 5 inside the cylindrical body 4, and secondly sealing two ends each of the bundle 5 and the cylindrical body 4 by potting agents 6 and 7 such as polyurethane resin. Headers 10 and 11, which are provided to an inlet 8 and an outlet 9 for body fluid, are arranged at each end of the cylindrical body 4. The headers 10 and 11 and the cylindrical body 4 are firmly connected by caps 12 and 13. Tubes 14 and 15 have each two ends. One end each of tubes 14 and 15 is connected to the inlet 8 or the outlet 9 for body fluid, with the other end each of the tubes 14 and 15 will be connected to a living body. In the inside of the cylindrical body 4, hollow fiber membrane lumens, which communicate with the inlet 8 and the outlet 9 for body fluid, and outside portions of the hollow fiber membrane, which communicate with the inlet tube 2 and the outlet tube 3, are separated.

The oxygenator includes microporous body fluid treatment membranes, such as hydrophobic and gas permeable membranes, having micropores with a pore size in the range of from several Å to 200 nm diameter, preferably from 10 nm to 80 nm diameter, and residing in a portion, which substantially affects properties of the membrane such as selective permeability, and permeation rate. The oxygenator has functions to purge carbon dioxide from blood and at the same time to introduce oxygen into the blood. Thus, the body fluid treatment membrane is concerned with gas transfer between blood and gas separated by the membranes. The body fluid treatment membranes used in the oxygenator are made of a material such as polyethylene, or polypropylene.

The plasma separation apparatus includes body fluid treatment membranes, which permeate plasma proteins, having micropores with a pore size in the range of from on the order of several ten nm to on the order of $\mu$m diameter, preferably from 100 nm to 1000 nm diameter in a portion, which substantially affects properties of the membrane such as selective permeability, and permeation rate. The plasma separation apparatus functions to separate plasma including proteins such as albumin, from blood by a filtering action. Therefore, the body fluid treatment membranes used in the plasma separation apparatus are concerned with filterable mass transfer of substances in blood from one side of the membrane to the other side of the membrane. Various kinds of materials are applicable in forming body fluid treatment membrane in a plasma separation apparatus.

A solubility parameter $\delta$ used in the present invention shows hydrophilicity of a material. The higher the parameter $\delta$ is, the higher the hydrophilicity is. On the other hand, the lower the parameter $\delta$ is, the higher the hydrophobicity is. A calculation method of the parameter $\delta$ is described in many publications such as 'Polymer Data Handbook—Basic edition', pgs. 591–593 (compiled by The Society of Polymer Science, Japan, and published by Baifukan in Jan. 30, 1986).

The microporous body fluid treatment membrane used in fabricating an artificial organ according to the present invention is made of a material having the solubility parameter $\delta$ of not more than 13 $(cal/cm^3)^{1/2}$. Moreover, the microporous membrane has a portion coated with a fat-soluble modifier. According to the present invention, since the membrane has the solubility parameter $\delta$ of not more than 13 $(cal/cm^3)^{1/2}$ before the membrane is coated with the fat-soluble modifier, the membrane firmly combines with the fat-soluble modifier such as vitamin E. Therefore, the fat-soluble modifier attached to the portion of the membrane has little tendency to be peeled off. As a result, the fat-soluble modifier works effectively.

A body fluid treatment membrane is generally coated with a fat-soluble modifier by contacting an organic solvent solution of fat-soluble modifier and then by drying the organic solvent off. Examples of organic solvents are, particularly, n-hexane, and 1,2,2-trichloro-1,2,2-trifluoroethane. However, as described above, when the body fluid treatment membrane is made of a hydrophobic material, the organic solution will penetrate into all micropores of the membrane. This will bring about a problem that the whole area of the membrane will be coated with the fat-soluble modifier.

[1] The manufacturing method of an artificial organ according to the present invention solves the above problem. The present invention provides a filling process, and a coating process. These processes enable only one side of the microporous hydrophobic membrane, or only the inside or the outside surface of the hollow fiber membrane, to be selectively coated with a fat-soluble modifier.

(1) Filling Process:

Filling process is a step to fill micropores of a body fluid treatment membrane with a filling solution. The filling solution has no or low solubility with a fat-soluble modifier solution, as well as giving no detrimental effect to the body fluid treatment membrane. When a solvent of fat-soluble modifier solution is n-hexane, or 1,2,2-trichloro-1,2,2-trifluoroethane, the filling solution is such as aqueous ethanol, or water, preferably water. Water is safe to organisms, and is easily disposed of as a waste. Moreover, it has a wide selection of organic solvents if water is adopted as the filling solution.

Detailed description on the filling process is now given by employing the hollow fiber membrane as the body fluid treatment membrane, and water as a filling solution.

A hollow fiber membrane of the body fluid treatment membrane is a member in the form of a hollow fiber. The membrane itself is made of a porous material. The hollow fiber membrane is generally classified into two kinds from the structural standpoint: uniform structure membrane and asymmetrical structure membrane. Either one of the above membranes may be adaptable to the present invention. The former, i.e., uniform structure membrane, has a uniform physical structure all over the membrane. The latter, i.e., asymmetrical structure membrane, has an uneven physical structure in such as pore diameters and support layers in cross sections, and has a dense layer on one of the inner and outer surfaces, or in a middle portion of the membrane, and a supporting layer having larger pores than those in the dense layer on the other surface or in a middle portion of the membrane. The dense layer is a portion, which allows substances to be selectively passed through, and affects properties of the membrane such as the passage rate of the substances. The supporting layer is a portion, which differs from the dense layer in a manner that it gives strength to the membrane enough to sustain inner resistance and filtration pressure.

According to the present invention, an inner surface defining a lumen, an outer surface, and a portion between the above two surfaces, no matter how many kinds of dense (or porous) layers it may consist, are hereinafter called as an inner surface, an outer surface, and a middle portion respectively. Micropores on the inner surface and on the outer surface refer to micropores residing in the proximity of the inner surface and in the proximity of the outer surface respectively. Micropores in the middle portion refer to micropores excluding those residing in the proximity of the inner and outer surfaces. The above definition, however, is not very clear.

According to the present invention, any of the filling, solvent removal, and coating processes may be performed either in the hollow fiber membranes alone or those arranged in a container, as seen in a dialyzer.

Filling micropores of hollow fiber membranes with water is not limited to a specific method. The hollow fiber membrane is filled with water, for example, in a manner that the outer surface or the inner surface of the hollow fiber membrane is contacted with water, either with pressure or without pressure. These methods are preferably employed, for example, when the pore size of the pores on the surface, which contacts water, of the hollow fiber membrane is relatively large (such as from 0.1 $\mu$m to 10 $\mu$m), and the membrane includes a hydrophilic polymer (when the hydrophilic polymer is polyvinylpyrrolidone, the polymer content should be between 3 wt % and 15 wt %). Another method is to allow hollow fiber membrane to contact an organic solvent, which is substituted with water (such as ethyl alcohol or methyl alcohol), or an aqueous solution of these solvents, with an appropriate pressure. After micropores are filled with an organic solvent or its aqueous solution, the solvent or its aqueous solution is replaced with water. The method to fill micropores first with an organic solvent or its aqueous solution and then to replace the solvent or the solution with water has an advantage in that the method ensures micropores all over the membrane will be filled with water. In either of the above methods, the appropriate pressure referred to means about not more than 2 $kg/cm^2$.

A method of bringing the outer surface of hollow fiber membrane into contact with water is to flow water along the outer surfaces of the membranes (i.e., in empty spaces defined by an inner surface of a cylindrical body and the outer surfaces of the membranes) after the hollow fiber membranes are incorporated into the cylindrical body to fabricate a dialyzer of hollow fiber membrane type as shown in FIG. 1. A method of bringing the inner surface of hollow fiber membrane into contact with water is to flow water in a lumen of the hollow fiber membrane. Another method is to allow the outer and inner surfaces of the membrane to contact with water and to fill micropores on both surfaces with water. In this method, either pressure or vacuum may be applied so as not to leave gas inside the hollow fiber membrane.

(2) Coating Process:

A coating process is to bring a portion of body fluid treatment membrane into contact with a fat-soluble modifier solution. The portion is specifically defined so as to be coated with fat-soluble modifier solution. For exemplary purposes, a process to employ hollow fiber membrane as body fluid treatment membrane, and water as a filling solution is now described.

When only the inner surface of the hollow fiber membrane is coated with a fat-soluble modifier, micropores in the middle portion and on the outer surface of the hollow fiber membrane is first filled with water, by such as bringing the outer surface of the hollow fiber membrane into contact with water as described above. Then, an organic solvent solution of fat-soluble modifier is flown through the lumen of the hollow fiber membrane of body fluid treatment membrane (or hollow fiber membrane functioning as dialysis membrane, in case of an dialyzer as shown in FIG. 1,) of an artificial organ so that the fat-soluble modifier is adhered to the inner surface of the hollow fiber membrane. Since micropores in the middle portion and the outer surface of the membrane are filled with water, a fat-soluble modifier and an organic solvent, which are insoluble or less soluble in water do not enter into the middle portion and the outer surface of the membrane. As a result, only the inner surface and its proximity of the membrane are coated with the fat-soluble modifier. By controlling the amount of filling solution to be filled in the inner surface and its proximity of the membrane, and also the amount of filling solution to be removed from the membrane during the liquid removal process described below, the ratio of the amount of fat-soluble modifier held on the inner surface of the hollow fiber membrane against the amount of fat-soluble modifier held on the whole area of the membrane may be controlled. If the amount of fat-soluble modifier held in the inner surface of the membrane exceeds 95 wt % of the total amount, the inner surface increases hydrophobic properties. This may cause the membrane to decrease its wettability with regard to body fluid.

When only the outer surface of the hollow fiber membrane is required to be coated with the fat-soluble modifier, micropores of the middle portion and the inner surface of the membrane are filled with water in advance by some appropriate means, such as by bringing the inner surface of the membrane into contact with water as described above. Then, preferably a liquid removal process is carried out as described below. Finally, an organic solvent solution of fat-soluble modifier is flown along the outside of the hollow fiber membrane so that the outer surface of the hollow fiber membrane is coated. Since micropores of the middle portion and the inner surface of the membrane are filled with water, the fat-soluble modifier and an organic solvent that are unsoluble or little soluble in water do not enter into the middle portion and the inner surface of the membrane. This results in that only the outer surface of the membrane is coated with a fat-soluble modifier with the middle portion and the inner surface of the membrane being left uncoated with the fat-soluble modifier.

In the coating process, if the inner surface of the hollow fiber membrane is contacted with an organic solvent solution for certain period of time, such as for between 30 seconds–60 minutes, preferably 1–10 minutes, the inner surface then comes to be more compatible with a fat-soluble modifier. This will favorably help increase the bonding strength between the hollow fiber membrane and the fat-soluble modifier.

In the coating process, after the organic solvent is removed, it is preferable that the coated inner surface of the hollow fiber membrane is dried by some means such as introducing air or an inert gas into the lumen of the hollow fiber membrane so that a film of the fat-soluble modifier is formed on the inner surface. In other words, after the organic solvent solution is removed, the remaining solvent is removed by evaporation, at a temperature, such as at 10–80° C., preferably 15–30° C., by introducing a gas, which does not affect the fat-soluble modifier, such as air, nitrogen, or carbon dioxide into the lumen of the hollow fiber membrane.

Moreover, a liquid removal process described below is preferably provided between the filling and coating processes. This liquid removal process will help the coating process to perform more efficiently.

(3) Liquid Removal Process:

Liquid removal process is to remove a filling solution from a surface of a portion of body fluid treatment membrane to be coated with a fat-soluble modifier.

After a filling process is performed, some filling solution may remain in the proximity (an inner surface and micropores therein) of the portion of the body fluid treatment membrane to be coated with the fat-soluble modifier. It is necessary to replace this filling solution by an organic solvent solution of fat-soluble modifier before a coating process is executed by means of introducing the organic solvent solution into a lumen of the hollow fiber membrane. This replacement will cause time consumption and waste of the organic solvent solution of fat-soluble modifier. Therefore, it is preferable to provide a liquid removal process before a coating process is performed so that the filling solution remained in the portion to be coated with the fat-soluble modifier should be removed.

As methods to remove a filling solution, a method to blow a gas, which is inert to filling solution, such as air or nitrogen gas, onto a surface to be coated at a temperature between 10 and 80° C., preferably between 20 and 40° C., is provided. The gas is preferably dried before applied.

When the inner surface of hollow fiber membrane is coated, a gas is blown into the lumen of the hollow fiber membrane, enabling removal of the filling solution remaining on the inner surface and in micropores therein. It is advantageous that a rapid removal of the remaining solution on the inner surface may be conducted and also a coated amount on the inner surface is controlled by adjusting the removal amount of the remaining solution.

When the outer surface of the hollow fiber membrane is coated, the filling solution remaining in micropores on the outer surface of the membrane may be removed by blowing a gas onto the outer surface of hollow fiber membrane directly. If hollow fiber membranes are incorporated into a cylindrical body to fabricate a dialyzer of hollow fiber membrane type as shown in FIG. 1, a gas is blown onto the outside of hollow fiber membrane (an open space defined by an inner surface of the cylindrical body and outer surfaces of hollow fiber membranes) This method will also remove a filling solution remaining in micropores on the outer surface of the membrane. The former method has an advantage in that a wider space between membranes enables to remove the remaining solution evenly, whereas the latter method has an advantage in that an easy removal operation brings about high productivity.

When the filling solution remaining in micropores on the outer surface is removed, the removal amount sometimes may be excessive. In this case, the filling solution filled in micropores not only in a middle portion, but also on the outer surface of hollow fiber membrane are removed. On the other hand, when the filling solution remaining in micropores on the inner surface is removed, filling solution only remaining on the inner surface is effectively removed. Therefore, the latter method will be a preferable aspect of the present invention.

Moreover, if a gas is blown onto the outside of hollow fiber membranes of a dialyzer of hollow fiber membrane type, an uneven removal of the filling solution in membranes is noticed between the outside and the center of a bundle of hollow fiber membranes. A removal amount of the filling solution left in the outside of a bundle of the membranes is generally greater than that in the center of the bundle. On the other hand, if a gas is blown into the lumen, an even removal of the filling solution may be performed. Therefore, the latter is preferably employed.

[2] Materials to be employed for body fluid treatment membrane are not specified in accordance with the present invention. As long as the solubility parameter δ is not more than 13 $(cal/cm^3)^{1/2}$, all materials may be employed. However, it is preferable to use at least one polymer selected from the group consisting of polyethylene (δ=7.70), polymethylmethacrylate (δ=9.10), polystyrene (δ=9.15), polypropylene (δ=9.40), polysulfone (δ=9.90), polyhydroxyethylmethacrylate (δ=10.00), nylon 66 (δ=11.18), cellulose diacetate (δ=11.35), polyacrylonitrile (δ=12.35), polyvinyl alcohol (δ=12.60), cellulose triacetate, ethylene-vinyl alcohol copolymer, and polycarbonate and the like.

When the body fluid treatment membrane is used for an dialyzer, polysulfone, cellulose triacetate, and polymethylmethacrylate are preferably employed. When the body fluid treatment membrane is used for an oxygenator, polypropylene, polysulfone, and polyethylene are preferably employed. When the body fluid treatment membrane is used for a plasmaseparation apparatus, polypropylene, polysulfone, and polyethylene are preferably employed. Moreover, the body fluid treatment membrane according to the present invention may include hydrophilic polymers such as polyvinylpyrrolidone, ethylene glycol, and hydroxyethylcellulose as one of constituents. When polysufone is employed as a material for body fluid treatment membrane, polyvinylpyrrolidone is preferably included as a hydrophilic polymer.

The fat-soluble modifier according to the present invention includes such as fat-soluble vitamins, and higher unsaturated fatty acids, for example, eicosapentaenoic acid, and docosahexaenoic acid. An example of fat-soluble vitamins is preferably vitamin E. Examples of vitamin E include tocopherols such as α-tocopherol, β-tocopherol, γ-tocopherol, and δ-tocopherol, tocotrienols such as α-tocotrienol, β-tocotrienol, γ-tocotrienol, and δ-tocotrienol, tocopherol derivatives such as tocopheryl acetate, and tocopheryl nicotinate.

Film thickness of vitamin E coatings is preferably between 0.001–1.0 μm, more preferably between 0.01–0.3 μm. If the film thickness is less than 0.001 μm, the vitamin E coating does not exhibit an inherent biocompatibility effect. On the other hand, if the film thickness is more than 1.0 μm, the vitamin E coating may decrease in dialysis performance.

The amount of vitamin E coating is preferably between 1–1000 $mg/m^2$, more preferably between 10–300 $mg/m^2$. If the amount of vitamin E coating is less than 1 $mg/m^2$, the coating becomes uneven. This results in decrease in biocompatibility effect. On the other hand, if the amount of vitamin E coating is more than 1000 $mg/m^2$, the film thickness comes to be undesirably thick. This results in elution of vitamin E or decrease in dialysis performance.

As a method of coating the body fluid treatment membrane with vitamin E, vitamin E is first dissolved in an organic solvent, preferably n-hexane, to obtain a solution of between 0.01–20 w/v %, more preferably of between 0.1–10 w/v %. Then, the resultant solution is contacted with the surface of the body fluid treatment membrane. (For example, in the case of an dialyzer as described in FIG. 1, a method is provided to coat the inner surface of the membrane where the vitamin E solution is introduced from an inlet 8 for body fluid and is discharged from an outlet 9 so that the inner surface of the dialysis membrane represented by a hollow fiber membrane bundle 5 contacts vitamin E solution; another method is also provided to coat the outer surface with vitamin E where the vitamin E solution is introduced from an inlet tube 2 for dialysis liquid and is discharged from an outlet tube 3 so that the outer surface of the dialysis membrane represented by the hollow fiber membrane bundle 5 contacts the vitamin E solution.) According to this method, a predetermined area of the surface may be specifically coated with vitamin E. Since an amount of vitamin E, which the other area of the surface is coated with, may be kept as small as possible, the coated amount of vitamin E on the body fluid treatment membrane will mostly depend on a vitamin E concentration in the vitamin E solution. This makes it possible to control the coated amount of vitamin E easily.

A preferable range of film thickness, coated amount, and concentration in an organic solvent described above with reference to Vitamin E are also applicable when other fat-soluble modifiers are employed.

Fat-soluble modifiers adhered to a portion of a surface of body fluid treatment membrane, which contacts body fluid, perform various physiological actions such as biological anti-oxidation, biomembrane stabilization, and platelet coagulation inhibition. Moreover, by applying fat-soluble modifiers to a portion of a surface of body fluid treatment membrane, which may not contact body fluid, hydrophobicity of the membrane is controlled so that the membrane may selectively adsorb such as hydrophobic substances.

Organic solvents to be employed in the present invention are any organic solvents, as long as they do not dissolve a synthetic polymer membrane, and are not or little soluble in a filling solution. When water is used as a filling solution, examples of organic solvents to be employed in the present invention include alcohols such as n-butanol, isobutanol, sec-butanol, and 2-ethylhexanol; ethers such as diethylether; hydrocarbons such as n-hexane; chlorinated hydrocarbon fluorides such as, trichlorofluoromethane, 1,1,2,2-tetrachloro-1,2-difluoroethane; perfluorocycloalkanes such as methyl fluoride, tetrafluoromethane, tetrafluoroethane, tetrafluoroethylene; perfluoromethylpropylcyclohexane, and perfluorobutylcyclohexane; and fluorinated hydrocarbons such as perfluorodecane, perfluoromethyldecalin, and perfluoroalkyltetrahydropyrane. Particularly, n-hexane, and 1,2, 2-trichloro-1,2,2-trifluoroethane are preferably employed.

When an aqueous methanol, or aqueous ethanol solution is used as the filling solution, organic solvents, which are hardly soluble in the aqueous ethanol solution, such as n-hexane and 1,2,2-trichloro-1,2,2-trifluoroethane are provided in the present invention. Particularly n-hexane is preferably employed. An aqueous methanol, or aqueous ethanol solution is employed in a concentration such that vitamin E is insoluble therein. The concentration of the aqueous methanol, or aqueous ethanol solution is preferably between 1–30 v/v %, more preferably between 5–20 v/v %.

Moreover, filling solutions including hydrophilic polymers such as polyvinylpyrrolidone, and polyethyleneglycol, or plasticizers for membranes such as glycerin may be employed. When a filling solution including a hydrophilic polymer is employed, wettability may be controlled, since it is possible to coat a specific area of a surface of a membrane with vitamin E and other areas with a hydrophilic polymer concurrently. Furthermore, when a filling solution including a plasticizer is employed, possible loss of a plasticizer included in a membrane may be prevented.

If the liquid removal process is provided and a remaining organic solvent is removed by evaporation by means of a gas, the organic solvent is preferably volatile and of low boiling point. In this case, an organic solvent such as n-hexane, or 1,2,2-trichloro-1,2,2-trifluoroethane is provided.

[3] A manufacturing method of an dialyzer of hollow fiber membrane type as a dialyzer has mainly been described. However, it should be understood that the present invention is not limited to the manufacturing method of an dialyzer of the kind and may also be used in manufacturing of other artificial organs having body fluid treatment membrane. The body fluid treatment membrane may be a flat membrane, as well as a hollow fiber member, as far as the solubility parameter δ of the membrane is not more than 13 $(cal/cm^3)^{1/2}$.

When body fluid treatment membrane is a flat membrane, a plate-and-frame type is proposed. The plate-and-frame type is formed by first applying either side of a plate-type supporting frame with flat membranes, and secondly stacking the supporting frame with flat membranes spaced from each other at an predetermined interval with spacers such that a module is fabricated. An inside portion defined by two inner surfaces of flat membranes facing with each other is regarded as a lumen of a hollow fiber membrane. An outer surface of a flat membrane facing an inner surface of a module housing is regarded as an outer surface of a hollow fiber membrane. Subsequent filling, solution removal, and coating processes will be performed with the inside portion between the flat membranes and the outer surface of a flat membrane in a similar manner as have been done with the lumen and the outer surface of the hollow fiber membrane respectively as described above. However, the plate-and-frame type may be more easily formed if a side of a membrane, which does not contact body fluid, undergoes filling process, and the other side, which contacts body fluid, is applied with a fat-soluble modifier solution with a brush or the like, before the module is fabricated. The present invention also includes the above aspect of the manufacturing method. It is also possible that the filling solution first fills the whole area of the membrane, then filling solution in the area to be coated with the fat-soluble modifier is only removed, and finally a fat-soluble modifier solution is applied to the area.

The present invention also provides a hollow fiber membrane and a dialyzer of a hollow fiber membrane type. The dialyzer is a structure of hollow fiber membranes, which utilizes dialysis and/or filtration operation in apparatuses such as a hemodialyzer, a hemodiafilter, and a hemofilter for treatments of chronic renal insufficiencies.

According to the present invention, a hollow fiber membrane comprises a microporous hollow fiber membrane having a surface which may not contact body fluid (body fluid flowing surface), and not less than 50 wt % of the total fat-soluble modifier is held on the body fluid contacting surface. Moreover, sieve coefficients of the membrane are not more than 0.4 when measured by a dextran with a molecular weight of 100,000, and not less than 0.5 when measured by another dextran with a molecular weight of 10,000.

The amount of the fat-soluble modifier held on the membrane surface, which may contact body fluid, is preferably between not less than 50 wt % and not more than 95 wt %, more preferably between not less than 60 wt % and not more than 90 wt %, of the total fat-soluble modifier contained in a hollow fibermembrane. If the amount of the fat-soluble modifier held on the surface, which may contact body fluid, is less than the lower limit (50 wt %), an excess amount of the fat-soluble modifier is held in other portions than the surface, which may contact body fluid. This results in decrease in water permeability. Moreover, if an appropriate amount of fat-soluble modifier is required to be held on the surface, which may contact body fluid, the amount of fat-soluble modifier to be applied is required to increase. This increase will result in increase in manufacturing cost. When the amount of fat-soluble modifier held on the surface, which may contact body fluid, exceeds the upper limit (95 wt %), the surface becomes more hydrophobic and less wettable.

In many dialyzers of hollow fiber membrane type, blood is generally flown along the inner surface of the hollow fiber membrane so that the predetermined amount of fat-soluble modifier is held on the inner surface of hollow fiber membrane. However, when blood is flown along the outer surface, the hollow fiber membrane of the present invention having the outer surface including a predetermined amount of fat-soluble modifier may be employed.

Substances such as uremic middle molecular-weight substances with a molecular weight of between 100 and 5,000, and β2-microglobulin (β2-MG) with a molecular weight of 11,800 are likely to be accumulated in a body during a long period of dialysis treatments. In order to remove these substances, it is required to enlarge the pore size of an membrane of a dialyzer. It, however, is not advantageous, since a body heavily loses active ingredients such as proteins in blood, for example, albumins during a dialysis treatment. The heavy loss of such active ingredients must be prevented. If the hollow fiber membrane according to the present invention, which has the sieve coefficients with the above mentioned ranges measured by using dextrans with molecular weights of 10,000 and 100,000 as indicators, is used, the above problems may be solved.

The sieve coefficients (when a fat-soluble modifier is held on a surface, which may contact body fluid) of the hollow fiber membrane of the present invention measured using dextrans are preferably not more than 0.1 and not less than 0.7 when dextrans with molecular weights of 100,000 and 10,000 are used respectively. If the sieve coefficient exceeds the upper limit (0.4) when the dextran with a molecular weight of 100,000 is used, the active ingredients in blood may be substantially eluted. On the other hand, if the sieve coefficient is below the lower limit (0.5) when the dextran with a molecular weight of 10,000 is used, useless substances such as middle molecular-weight substances are not fully removed.

The hollow fiber membrane according to the present invention is mainly made of a synthetic polymer substrate, which forms micropores. The membrane may contain mixtures such as pore forming agents. The synthetic polymer substrate to be employed in the present invention is preferably a synthetic polymer having a solubility parameter δ of not more than 13 (cal/cm$^3$)$^{1/2}$. The membrane made of this kind of synthetic polymer has excellent compatibility with fat-soluble modifiers such as fat-soluble vitamins. Moreover, the hollow fiber membrane holds a fat-soluble modifier more easily. Examples of the synthetic polymers include polyethylene (δ=7.70), polymethylmethacrylate (δ=9.10), polystyrene (δ=9.15), polypropylene (δ=9.40), polysulfone (δ=9.90), polyhydroxyethylmethacrylate (δ=10.00), nylon 66 (δ=11.18), cellulose diacetate (δ=11.35), polyacrylonitrile (δ=12.35), polyvinyl alcohol (δ=12.60), cellulose triacetate, ethylene-vinyl alcohol copolymer, and polycarbonate. These substances may be used discretely or in mixtures thereof.

The solubility parameter δ is preferably between not less than 9.50 and not more than 12.

Fat-soluble vitamins, and fatty acids such as fish oils are provided and preferably used as fat-soluble modifiers to be employed in the hollow fiber membrane of the present invention. Fat-soluble vitamins and fatty acids are biologically originated substances and have various physiological actions. Fat-soluble vitamins are preferably, for example, vitamin A, vitamin D, vitamin E, vitamin K, and quinones. Among them, vitamin E is preferable. Examples of vitamin E include tocopherols such as α-tocopherol, as α-tocopheryl acetate, α-tocopheryl nicotinate, β-tocopherol, γ-tocopherol, and δ-tocopherol. Examples of fish oils include highly unsaturated fatty acids such as eicosapentaenoic acid, and docosahexaenoic acid. These highly unsaturated fatty acids provide antithrombotic properties, and lower hyperlipemia. Coated amount of fat-soluble modifier is preferably between 1–1000 mg/m$^2$, more preferably between 10–300 mg/m$^2$. If the fat-soluble modifier is not more than 1 mg/m$^2$, coated film is liable to be uneven. This results in decrease in biocompatibility. On the other hand, if the coated amount of fat-soluble modifier is not less than 1000 mg/m$^2$, the coated film becomes thick. This may cause the fat-soluble modifier to elute, followed by decrease of dialysis performance in some cases.

An amount of a fat-soluble modifier residing in a membrane may be found by various methods such as infrared spectroscopy, X-ray electron spectroscopy, secondary ion mass spectroscopic analysis, nuclear magnetic resonance spectrometry, various extraction methods, and combinations thereof.

A hollow fiber membrane having the above mentioned specific sieve coefficients for an dialyzer has a membrane structure such that pores in the outer, inner surfaces, and a cross section of the membrane may be observed or nearly observed by a scanning electron micrograph with a magnification of 10,000. If a module of hollow fiber membrane is fabricated according to the prior art, and is applied with a solution of a fat-soluble modifier such as vitamin E in a lower alcohol such as ethanol or methanol, the solution may enter into pores all over the membrane. This means that all surfaces of the network structure forming pores are coated with vitamin E. This causes vast amount of vitamin E is required. Moreover, since vitamin E is adhered to all over the membrane, hydrophobicity of the membrane increases. This may decrease water permeation performance of the membrane with respect to body fluid or dialysis liquid. Therefore, as described above, the advantageous manufacturing method of the hollow fiber membrane according to the present invention may utilize a coating method of a fat-soluble modifier, including filling, and coating processes.

[4] An embodiment of coating the inner surface of the membrane with vitamin E will be now described as an exemplary example of a manufacturing method of a hollow fiber membrane of the present invention.

(1) Filling Process:

As shown in FIG. 1, hollow fiber membranes 5 are incorporated into a cylindrical body 4 to fabricate a dialyzer 1 of hollow fiber membrane type. A 50 v/v % aqueous ethanol solution is introduced from an inlet 8 for body fluid and an inlet tube 2 for dialysis liquid to fill micropores residing in the membranes. Then, water is introduced from an inlet 8 for body fluid and an inlet tube 2 for dialysis liquid to replace an aqueous solution with water, resulting in filling micropores residing in the membranes with water.

(2) Liquid Removal Process:

By blowing air with a temperature of 30° C. from an inlet 8 for body fluid into a lumen of a hollow fiber membrane, water remaining in micropores in an inner surface of the hollow fiber membrane is removed.

(3) Coating Process:

After the lumen of the hollow fiber membrane is filled with an n-hexane solution of vitamin E, and is left to stand for 2 minutes, the solution is discharged. Then, a nitrogen gas is blown into the lumen such that the inner surface of the membrane is dried by removing the remaining n-hexane completely.

Meanwhile, it is possible that the amount of the remaining water has been controlled by utilizing various air flow rates in the above liquid removal process. If it has been performed, the amount of the fat-soluble modifier held on the surface of the membrane, which may contact body fluid, may be controlled in this process so as to be not less than 50 wt %, preferably between not less than 50 wt % and not more than 95 wt %, of the total fat-soluble modifier amount included in the membrane.

Moreover, in the above manufacturing method of an dialyzer according to the present invention, it is a preferable aspect of the present invention that body fluid treatment membrane comprises a hollow fiber membrane of the present invention.

Furthermore, as a preferable manufacturing method of an dialyzer of hollow fiber membrane type according to the present invention, the above mentioned manufacturing method of artificial organs according to the present invention may be applied.

Embodiments of the present invention will now be described in more detail with reference to the appended drawing.

EXAMPLE 1

10,300 pieces of polysulfone-made hollow fiber membrane having an inner diameter of 200 μm, an outer diameter of 280 μm (pore sizes of 3 nm diameter of pores in an inner surface, and of 500 nm of pores in an outer surface), a length of 24 cm, and a solubility parameter δ of 9.90 (cal/cm$^3$)$^{1/2}$ was inserted into a cylindrical body as shown in FIG. 1. Then, either end of the body was fixed by polyurethane-based potting agents 6 and 7, and attached with headers 10 and 11, and mounted with caps 12 and 13 so as to obtain a dialyzer (an artificial kidney) 1 with a membrane surface area of 1.5 m$^2$.

Next, water was introduced into micropores of the hollow fiber membrane at the rate of 500 ml/min from an inlet for dialysis liquid for one minute so that micropores were filled with water. Then, after almost all water residing in the outside of the hollow fiber membrane was discharged by gravitation, a small amount of water remained in the lumen of the hollow fiber membrane was expelled by blowing air in from the header for 10 minutes.

A vitamin E solution in n-hexane with a concentration of 2 w/v % was prepared by dissolving 2.0 g of vitamin E (dl-α-tocopherol) in 100 ml of n-hexane. After a 50 ml syringe was connected to a tube 14 communicating with an outlet 9 for body fluid, the tip of the syringe was placed in the vitamin E solution. By actuating a plunger of the syringe, the lumen of the hollow fiber membrane of the dialyzer was filled with the vitamin E solution. The hollow fiber membrane filled with the vitamin E was left to stand for 2 minutes. Then, after most vitamin E solution was discharged, a nitrogen gas was blown at 60° C. into the inside of the member to dry it by expelling the remaining n-hexane. As a result, the inner surface of the dialyzer was coated with 23.8 mg/m2 of vitamin E.

EXAMPLE 2

A dialyzer was manufactured following the same steps as those taken when Example 1 was manufactured, except that the concentration of a vitamin E solution in n-hexane was controlled to be 5 w/v %. The amount of vitamin E, with which the inside of the dialyzer has been coated, was 55.2 $mg/m^2$.

COMPARATIVE EXAMPLE 1

For comparison purposes, a dialyzer was manufactured following the same steps as those taken when Example 1 was manufactured, except that the water filling process has not been applied. When the coating process with vitamin E was taken, it was noticed that a vitamin E solution introduced into the lumen of the hollow fiber membrane was filtered out into an outside of the membrane. The amount of vitamin E, which the inside of the dialyzer has been coated with, was 115.7 $mg/m^2$.

COMPARATIVE EXAMPLE 2

A dialyzer was manufactured following the same steps as those taken when Example 1 was manufactured, except that the concentration of a vitamin E solution in n-hexane was controlled to be 5 w/v %. When the coating process with vitamin E was taken, it was noticed that a vitamin E solution introduced into the lumen of the hollow fiber membrane was filtered out into the outside of the membrane. The amount of vitamin E, with which the inside of the dialyzer has been coated, was 298.6 $mg/m^2$.

EXAMPLE 3

10,300 pieces of polysulfone hollow fiber membrane having an inner diameter of 200 μm, an outer diameter of 280 μm, a solubility parameter $\delta = 9.90$ $(cal/cm^3)^{1/2}$, and sieve coefficients measured using dextrans, which are described later, (of 0.1 when a dextran with a molecular weight of 100,000 was used, and of 0.9 when another dextran with a molecular weight of 10,000 was used) were inserted into a cylindrical body as shown in FIG. 1. After either end of the body was fixed by polyurethane-based potting agents 6 and 7, the ends were also attached with headers 10 and 11, and then mounted with caps 12 and 13 so as to obtain a dialyzer (an dialyzer) 1 with an inner surface area of 1.5 $m^2$.

Next, water was introduced into micropores of the hollow fiber membrane at the rate of 500 ml/min from an inlet for dialysis liquid for one minute so that micropores were filled with water. Then, after most water residing in the outside of the hollow fiber membrane was discharged by gravitation, all water remained in the lumen of the hollow fiber membrane was expelled by blowing air in from the header for 10 minutes.

A vitamin E solution in n-hexane with a concentration of 4 w/v % was prepared by dissolving 4.0 g of vitamin E (dl-α-tocopherol) in 100 ml of n-hexane. After a 50 ml syringe was connected to a tube 14 communicating with an outlet 9 for body fluid, the tip of the syringe is placed in the vitamin E solution. By actuating a plunger of the syringe, a lumen of the hollow fiber membrane of the dialyzer was filled with the vitamin E solution, and was left to stand for 2 minutes. Then, after most vitamin E solution was discharged from the dialyzer, a nitrogen gas at 60° C. was blown in so as to dry an inner surface of the member by expelling the remaining n-hexane.

Total amount of vitamin E (dl-α-tocopherol) fixed on the above hollow fiber membrane was measured in the following method:

In order to measure the total fixed amount of vitamin E (dl-α-tocopherol) on the above hollow fiber membrane, the hollow fiber membranes (300 pieces with 15 cm long each) were first cut into 1.5 cm. The resultant cut pieces were then sonicated in 20 ml of ethanol for 60 minutes to obtain a vitamin E extract. Finally the amount of vitamin E extracted in the ethanol was measured quantitatively by liquid chromatography under the conditions described below. The surface area of the membrane was found from an average inner diameter of hollow fiber membrane, the number and length of membranes.

Measurement of the amount of vitamin E fixed on the inner surface of the hollow fiber membrane was performed as follows:

A mini-module with a membrane surface of 300 $cm^2$ employing the above coated hollow fiber membrane was fabricated (341 pieces of fibers each with a length of 14 cm). Urethane resin (main agent: C-4403, 2300 cps/25° C., NIPPON POLYURETHANE INDUSTRY, CO., curing agent: N-4235, 1100 cps/25° C., NIPPON POLYURETHANE INDUSTRY CO.) for potting purposes was injected from the outer surface of the hollow fiber membrane of the mini-module such that the micropores of the hollow fiber membrane were filled with the urethane resin, and the inner surface were not. Then, 15 ml of ethanol was introduced into the inner surfaces of the hollow fiber membrane, i.e., the lumens of the hollow fiber membrane in the mini-module, and was circulated at a flow rate of 10 ml/min. for 4 hours, so as to extract vitamin E. The amount of vitamin E extracted in the ethanol was measured quantitatively by a liquid chromatography as described below.

| Column: | CAPCELL PAK SG120 |
| Mobile phase: | methanol:water = 97:3 |
| Flow rate: | 1.2 ml/min |
| Detector: | UV284 nm |

Measurements showed that the amount of vitamin E fixed to the inner surface was 33.0 $mg/m^2$, i.e., 72% of the total fixed amount, whereas the total fixed amount of vitamin E was 45.8 $mg/m^2$.

COMPARATIVE EXAMPLE 3

For comparison purposes, a dialyzer was manufactured following the same steps as those taken when Example 3 was manufactured, except that the water filling process was not applied. When the coating process with vitamin E was performed, it was noticed that a vitamin E solution introduced into the lumen of the hollow fiber membrane was filtered out into the outside of the membrane. The amount of vitamin E, with which the inside of the dialyzer has been coated(the total coated amount of vitamin E), was 353 mg/m². Moreover, a mini-module similar to that of Example 3 was also manufactured, and the vitamin E was measured. The coated amount of vitamin E was 116 mg/m².

<Measurements of Sieve Coefficients:>

The sieve coefficients of polysulfone-based hollow fiber membrane, which was employed in Example 3 and Comparative Example 3, were measured by the following method:

Dextrans T10 and T40 (available from Pharmacia) were dissolved in a physiological saline to obtain 10 g/l solution.

Next, a mini-module having a membrane surface of 100 cm² per hollow fiber membrane was fabricated. The above dextrans solution was circulated in a lumen of the hollow fiber membrane at a linear velocity of 100 cm/min. The filtration was performed under low pressure (100 mmHg). Sampling operations were performed from the above dextrans solution during circulation, and also from the filtered-out solutions (at 3 points of an inlet (IN), and an outlet (OUT) of the module, and filtrate (F) on the solution). On each example, relationship between molecular weight and holding capacity was found by a gel permeation chromatograph (GPC) under the conditions described below. Based on the relationship, sieve coefficient SC (=$2C_F/(C_{IN}+C_{OUT})$, wherein C stands for a concentration, and small affixed letters designate sampling locations), is calculated from each dextran concentration at IN, OUT, and F locations. The dependability of SC (molecular weight cut-off curve) was found.

<Measurements by GPC:>

Measuring Instrument: High performance GPC system (Shodex GPC SYSTEM-11, manufactured by Showa Denko K.K.)

Column: Shodex GPC column for general use of Ohpak high performance type (Ohpak KB-803, manufactured by Showa Denko K.K.)×2+precolumn (Ohpak KB-800p, manufactured by Showa Denko K.k.)

Mobile Phase: physiological saline

All examples were diluted 20 times prior to measurements.

Test 1

Clearances of vitamin $B_{12}$ were measured, using dialyzers of Examples 1 and 3, and also of Comparative Examples 1 and 3. On the side of blood, acetic acid dialysis solution including vitamin $B_{12}$ with a concentration of 2 mg/dl was flown at the flow rate of 200 ml/min. On the side of dialysis solution, acetic acid dialysis solution was flown at the flow rate of 500 ml/min. After above solution was kept flowing under the above conditions for 5 minutes while keeping a constant filtration rate to be 15 ml/min, flowing amount of blood at the inlet ($Q_{Bi}$), concentration of blood at the inlet ($C_{Bi}$), flowing amount of blood at the outlet ($Q_{Bo}$), concentration of blood at the outlet ($C_{Bo}$) were found. Based on these measurements, each clearance was calculated by the following formula:

$$\text{Clearance } (C_L)=(C_{Bi} \times Q_{Bi}-C_{Bo} \times Q_{Bo})/C_{Bi}$$

Measurements were performed at 37° C. Concentration was found by measuring absorption of light with a wavelength of 360 nm.

Test results showed that the clearances of vitamin $B_{12}$ were 132 ml/min for Example 1, 132 ml/min for Example 3, 93 ml/min for Comparative Example 1, and 95 ml/min for Comparative Example 3.

As described above, the present invention comprised of a manufacturing method of an artificial organ comprising a microporous body fluid treatment membrane, which is formed of a material with a solubility parameter δ of not more than 13 (cal/cm³)$^{1/2}$, and has a portion coated with a fat-soluble modifier, wherein the manufacturing method is comprised of the steps: filling micropores in the body fluid treatment membrane with a filling solution, which has no or little solubility with a fat-soluble modifier solution; and coating a portion of the membrane to be coated with the fat-soluble modifier by contacting the fat-soluble modifier solution. In the prior art manufacturing method, which adopts only coating process of a fat-soluble modifier without utilizing a filling process, an organic solvent solution of the fat-soluble modifier permeates the membrane such that the whole membrane including a surface on the front side necessary to be coated, a middle section, and a surface on the reverse side is coated with the fat-soluble modifier. On the other hand, according to the manufacturing method of the present invention, only necessary portion of the membrane is coated with the fat-soluble modifier. This may decrease the necessary amount of the fat-soluble modifier, with which the membrane is coated.

Moreover, the present invention may improve the concentration of the fat-soluble modifier in its organic solvent solution, pressure at various processes, and difficulty of controlling a coated amount variance depending on factors such as compatibility, and permeation properties of body fluid treatment membrane against an organic solvent used.

Furthermore, in the prior art manufacturing method, the membrane is totally coated with hydrophobic vitamin E so that the membrane increases in hydrophobicity as a whole. This high hydrophobicity brings about a problem that, as filtration amount of water decreases, and also as compatibility with a dialysis solution decreases, dialysis properties decreases. On the other hand, according to the present invention, the original effectiveness of a fat-soluble modifier may be maintained without lowering the dialysis performance, since only the necessary portions (such as the inner surface of the hollow fiber membrane) may be coated with a fat-soluble modifier.

The present invention comprised of a microporous hollow fiber membrane having a surface, which may contact body fluid, and includes a fat-soluble modifier, is further comprised of the hollow fiber membrane, wherein sieve coefficients are not more than 0.4 when a dextran with a molecular weight of 100,000 is used, and not less than 0.5 when another dextran with a molecular weight of 10,000 is used, and that not less than 50 wt % of total fat-soluble modifier, with which the membrane has been coated, are held on the portion of the membrane, which may contact body fluid. Based on the above characteristics, the present invention will improve removal of substances accumulated in a body by a long period of dialysis treatments such as a substance with a molecular weight of between 100 and 5,000, a uremic substance with a middle molecular weight, and β2-microglobuline (β2-MG) with a molecular weight of 11,800. The present invention also prevents a heavy loss of proteins such as albumin, which is an active ingredient of blood, and improves biocompatibility.

Moreover, the hollow fiber membrane is formed of a synthetic polymer substrate, preferably with a solubility parameter of not more than 13 (cal/cm³)$^{1/2}$, so that the membrane has an excellent compatibility with a fat-soluble modifier. The fat-soluble modifier, preferably a fat-soluble vitamin, may prevent generation of active oxygen.

Furthermore, the present invention comprising an dialyzer of hollow fiber membrane type having the above described hollow fiber membrane may decrease occurrence of complications caused by a long period of dialysis treatments for a patient affected with chronic renal insufficiencies.

By the manufacturing method of an artificial organ according to the present invention, the artificial organ with the following characteristics may be obtained:

A body fluid treatment membrane is formed of the above described hollow fiber membrane;

Substances such as a uremic substance with a middle molecular weight, β2-microgloburin with a molecular weight of 11,800 (β2-MG) are removed;

A heavy loss of proteins such as albumin, which is an active ingredient of blood, is prevented; and Biocompatibility is improved.

When the above described dialyzer of hollow fiber membrane type according to the present invention is fabricated following a manufacturing method of an artificial organ of the present invention, lowering of dialysis performance resulted from lowering of filtration amount of water, and lowering of compatibility with dialysis solution may be prevented.

What is claimed is:

1. A hollow fiber membrane, comprising an inner surface with micropores, an outer surface with micropores, a middle portion with micropores between the inner surface and outer surface, and a lumen region contained within the inner surface, said hollow fiber membrane being formed of a synthetic polymer substrate having a solubility parameter δ of not more than 13 $(cal/cm^3)^{1/2}$, and wherein not less than 50 wt % and up to 95 wt % of a fat-soluble vitamin or a higher unsaturated fatty acid included in said hollow fiber membrane is held on the outer surface or inner surface, which contacts body fluid;

wherein the outer surface or inner surface that includes the fat soluble-vitamin or the higher unsaturated fatty acid is produced by:
  filling micropores of said membrane with a filling solution which has no or little solubility with a fat-soluble modifier solution;
  removing the filling solution from a portion of the membrane to be coated by blowing air into the lumen region of the membrane to be coated, wherein the amount of fat soluble-vitamin or higher unsaturated fatty acid on the outer surface or inner surface is controlled by adjusting the amount of the filling solution removed; and
  coating the inner surface of said membrane with the fat-soluble vitamin or a higher unsaturated fatty acid by contacting said membrane with said fat-soluble modifier solution; wherein
    sieve coefficients of the membrane measured by dextrans are:
      not more than 0.4 when a dextran with a molecular weight of 100,000 is employed; and
      not less than 0.5 when another dextran with a molecular weight of 10,000 is employed.

2. A dialyzer comprising a hollow fiber membrane, a body fluid passage, a dialysis fluid passage, wherein a body fluid flowing in said body fluid passage contacts a dialysis fluid flowing in said dialysis fluid passage through said membrane, wherein uremic middle molecular-weight substances with a molecular weight of between 100 and 5000 and β2-microglobulin may be transferred and removed, while albumins are not transferred or heavily lost, wherein said hollow fiber membrane is the hollow fiber membrane as set forth in claim 1.

* * * * *